United States Patent [19]

Salpekar

[11] Patent Number: 5,364,601
[45] Date of Patent: Nov. 15, 1994

[54] TREATING OF CONTACT LENSES WITH COMPOSITIONS COMPRISING PVP-H2O2

[75] Inventor: Anil Salpekar, Pittsford, N.Y.

[73] Assignee: Bausch & Lomb Incorporated, Rochester, N.Y.

[21] Appl. No.: 998,507

[22] Filed: Dec. 30, 1992

[51] Int. Cl.$^5$ ............................ A61L 2/00; A61L 9/00
[52] U.S. Cl. ......................................... 422/28; 422/30; 422/34; 424/78.04; 424/616; 514/2
[58] Field of Search ..................... 422/28, 30, 34; 424/78.04, 457, 460, 616, 94.4; 514/839–840, 2; 252/106

[56] References Cited

U.S. PATENT DOCUMENTS

| | | | |
|---|---|---|---|
| Re. 32,672 | 5/1988 | Huth et al. | 252/95 |
| 3,549,747 | 12/1970 | Krezanoski | 424/78.04 |
| 3,912,451 | 10/1975 | Gaglia, Jr. | 21/158 |
| 4,525,346 | 6/1985 | Stark | 424/80 |
| 4,568,517 | 3/1986 | Kaspar et al. | 422/30 |
| 4,585,488 | 4/1986 | Giefer | 134/27 |
| 4,748,992 | 6/1988 | Giefer | 134/84 |
| 4,767,559 | 8/1988 | Kruse et al. | 252/106 |
| 5,008,106 | 4/1991 | Merianos et al. | 424/80 |
| 5,011,661 | 4/1991 | Schafer et al. | 422/30 |
| 5,130,124 | 7/1992 | Merianos et al. | 424/53 |
| 5,145,644 | 9/1992 | Park et al. | 422/28 |

OTHER PUBLICATIONS

The Condensed Chemical Dictionary, 8th Edition, Reinhold Publishing Corp., 1971, p. 412.

*Primary Examiner*—Robert J. Warden
*Assistant Examiner*—Krisanne M. Thornton
*Attorney, Agent, or Firm*—Craig E. Larson

[57] ABSTRACT

A composition and method for disinfecting and cleaning contact lenses is taught wherein the lenses are contacted with a composition including solid PVP-$H_2O_2$ and a solid neutralizing component for neutralizing residual $H_2O_2$. The composition may also include a preserved saline solution in which the composition components are contacted with the lenses substantially simultaneously. The neutralizer component may be a metal catalyst, a chemical salt or an enzyme. The effect of the neutralizer component may be delayed until after disinfecting is complete.

11 Claims, No Drawings

TREATING OF CONTACT LENSES WITH COMPOSITIONS COMPRISING PVP-H2O2

FIELD OF THE INVENTION

The invention relates to methods and compositions for cleaning and disinfecting of contact lenses that employ hydrogen peroxide to disinfect the contact lenses, followed by neutralizing of residual hydrogen peroxide after disinfecting is complete. More particularly, the invention relates to combinations of a solid source of hydrogen peroxide, a complex of polyvinylpyrrolidone and hydrogen peroxide (PVP-$H_2O_2$), with various neutralizing compositions and/or cleaning compositions that improve care and maintenance of soft contact lenses and reduce complexity of lens care regimens.

BACKGROUND OF THE INVENTION

The use of hydrogen peroxide systems for disinfecting soft contact lenses is well known for its efficacy. Conventional disinfecting processes employing $H_2O_2$ utilize either $H_2O_2$ itself or a compound that yields $H_2O_2$ such as a metal peroxide, percarbonate, alkylperoxide or the like. Most processes employ $H_2O_2$ in a 3-5% by weight aqueous solution. Recently, Merianos et al. in U.S. Pat. No. 5,008,106, described a solid, anhydrous complex of PVP-$H_2O_2$ that may be utilized to generate $H_2O_2$ solution for disinfecting contact lenses.

Hydrogen peroxide disinfecting, however, requires that residual hydrogen peroxide remaining on the lenses after disinfecting must be neutralized or decomposed to a biologically inert state before the disinfected lenses may be placed on the eyes. Significant residual $H_2O_2$ remaining on the lenses results in eye irritation, generally manifested by stinging sensations.

A number of neutralizing or reducing agents and methods are known in the art. Each neutralizing method is typically combined with a conventional aqueous solution source of $H_2O_2$ for disinfecting the lenses. The prior art combinations with $H_2O_2$ solution have certain disadvantages. For example, U.S. Pat. No. 3,912,451 teaches neutralizing residual hydrogen peroxide by contacting the $H_2O_2$ disinfecting solution and lenses therein with a metal, such as platinum, that catalyzes decomposition. A difficulty arising from this system is that neither the $H_2O_2$ solution, because of its strong oxidizing character, nor the solid form of the catalyst allow for the presence of a preservative. The resulting $H_2O_2$ residual-free solution holding the lenses is not preserved. Thus, the solution and lenses are at risk of contamination and reinfection unless additional steps and solutions or compositions are added to the process.

Other agents are known in the art for decomposing hydrogen peroxide in contact lens disinfecting systems. Of particular interest, because it acts at a faster, more convenient rate, is the use of an enzyme, such as catalase. For example, U.S. Pat. Nos. 4,748,992 and 4,585,488 report effective decomposition of $H_2O_2$ taking place within a few minutes of introduction of catalase. The process of patent '488 requires sterilizing a contact lens with an aqueous solution of $H_2O_2$ and subsequently contacting the lens with an isotonic solution of dissolved catalase. Catalase in tablet form may be utilized but the $H_2O_2$ source remains a conventional aqueous solution.

In addition to characteristics of the disinfecting/neutralizing chemicals per se, a major goal in designing lens care formulations relates to their methods of use. It is widely accepted that regimens for disinfecting and cleaning contact lenses must be as simple as possible to encourage lens wearers to comply with the care regimens as a matter of avoiding adverse health effects due to contaminated lenses. Any simplification in a regimen, such as by combining processing steps, combining chemicals, adding separate components at the same time, or the like is generally advantageous in seeking to achieve patient compliance.

Simplyifying lens care regimens by combining disinfecting and neutralizing components remains difficult to achieve because of the difficulty of balancing the relative reaction rates of the disinfecting and neutralizing processes. A difficulty with fast neutralizing of $H_2O_2$ systems, such as catalase, is that the lenses to be effectively disinfected, must be exposed to a relatively high concentration of $H_2O_2$ for a significant, finite period of time in order to achieve disinfecting before neutralizing proceeds significantly. The time required for disinfection is generally dependent upon the concentration of hydrogen peroxide utilized, requiring on the order of two hours at 1.0 weight percent $H_2O_2$ while only five minutes at 3.0% by weight hydrogen peroxide. Since it is preferred that $H_2O_2$ concentration be as low as possible, it is evident that if one desires, as a matter of simplifying a lens care regimen, to treat lenses simultaneously with hydrogen peroxide and a fast acting neutralizer, such as catalase, it is necessary to employ the neutralizer with care. In fact, it is preferable to delay the effective release of such a neutralizer in order to allow adequate time to achieve disinfecting and, thereafter, obtain substantially complete neutralization of the disinfecting hydrogen peroxide component.

A number of proposals have been made for delaying release of the neutralizing agent until after the disinfecting step is at least substantially complete. Some of these proposals include combining regimen steps and system components. Kruse, et al., in U.S. Pat. No. 4,767,559, form a one step cleaning/disinfecting tablet that includes a solid outer layer that is the disinfecting component and a solid core that comprises the neutralizing agent. The disinfecting agent may be any acid-reacting $H_2O_2$ generating compound such as potassium persulfate, melamine perhydrate and is, preferably, urea peroxdhydrate. The core neutralizing agent comprises a reducing agent, such as ascorbic acid or glucose or an enzyme, such as catalase. In operation, the disinfecting agent first dissolves, followed by the core dissolving thereby neutralizing the residual disinfecting agent. A difficulty with this product is that the process for making the outer layered/core tablet is complex which adds significant cost such that a commercial product has yet been successfully marketed using this concept.

Kaspar et al, in U.S. Pat. No. 4,568,517, describe simultaneously contacting lenses with a hydrogen peroxide solution and a neutralizing agent, preferably sodium thiosulfate or sodium sulfite, in a solid form such as a tablet. The neutralizer agent is provided with a coating which dissolves gradually to release neutralizer only after the disinfecting period has elapsed. The $H_2O_2$ solution is transformed in situ into a buffered saline lens storage solution having a pH of 6.5-8.5 and a tonicity of 200-450 milliosmol per kg solution. A difficulty with the preferred sodium thiosulfate tablet is that it is large in size, making this approach unpractical.

A further difficulty with controlled release systems is that of providing adequate flexibility in release times and profiles, as well as good uniformity of release. Schäfer et al., in U.S. Pat. No.5,011,661, describes controlled release of neutralizing agent into a peroxide system through an insoluble, yet semi-permeable membrane coating or capsule. The membrane comprises various polymers and triacetin for controlling release. Park et al., in U.S. Pat. No. 5,145,644, describes a method for coating a tablet with a controlled release water soluble polymer employing a water and ketone solvent. The ketone containing solvent is said to produce increased uniformity of coating.

A further aspect of proper contact lens care and maintenance is cleaning of the lenses of debris and contaminants that accumulate from daily wear in the eyes. As is well known, proteins, such as lysozyme, and oily substances, such as lipids, deposit on the lens during wear, eventually interfering with comfort and visual acuity. Typically, surfactants are combined to form a daily cleaner for removing the lipid contaminants. Proteolytic enzymes are employed on a weekly basis for removing protein contaminants.

Since cleaning regimens do not provide sufficient disinfecting, separate disinfecting steps always follow cleaning before the lenses are placed on the eye or in storage. In general, it is thought that the disinfecting regimens do not provide significant cleaning. Thus, forming a complete lens care regimen requires ensuring that the various cleaning regimens are compatible with a disinfecting regimen, such as the $H_2O_2$/neutralizer system described above and of particular interest herein.

Hydrogen peroxide disinfecting/neutralizing systems and methods remain relatively complex and require somewhat inconvenient regimens, making combination with cleaning systems difficult. Having a complete lens care disinfecting system in a single, dry package that need only be combined with a preserved saline solution would be advantageous over prior art systems for forming less complex lens care regimens. Such a system would be particularly advantageous where the disinfecting system itself provides significant cleaning efficacy and is otherwise particularly amenable to combination with conventional cleaning surfactants and protelytic enzymes in a convenient delivery package. Such a system would promote compliance with lens care regimens by providing convenient packaging and delivery systems, as well as a reduction in the number of regimen steps required and solutions involved that must be mixed and maintained.

SUMMARY OF THE INVENTION

The invention is a disinfecting and cleaning composition for articles such as contact lenses, comprising an oxidizing component, in an amount sufficient for disinfecting, that is a solid complex of polyvinylpyrrolidone and hydrogen peroxide ($PVP-H_2O_2$); and, a solid neutralizer component for neutralizing residual oxidizing agent after disinfecting. Both components are in dry, solid forms and are substantially simultaneously contacted with the object to be sterilized which is submerged in an aqueous medium, preferably preserved with an antimicrobial composition.

Preferably, the $PVP-H_2O_2$ complex comprises 5-40% by weight $H_2O_2$. The $PVP-H_2O_2$ complex is in the form of a solid tablet, granules or powder, suitable for combination with a solid neutralizer component which may be included in a dry package in various forms, preferably in a capsule. The neutralizer component may be a metal catalyst, selected from Groups 4, 5 or 6 of the Periodic Table, such as Pt, Pd, Ru, Fr, Cr, or the like; a chemical compound such as pyruvic acid, sodium pyruvate, sodium thiosulfate, thiourea, sodium sulfate, ascorbic acid or the like; or an enzyme, such as catalase, peroxidase or the like.

A means may be employed for delaying release of neutralizer, preferably comprising encapsulating the neutralizer component in a capsule that disintegrates or decomposes in the aqueous medium after a finite period of time such that disinfecting by $H_2O_2$ is achieved prior to significant neutralization by the neutralizer. Preferably, the capsule comprises a gelatin.

The invention also includes a method of disinfecting and cleaning contact lenses, comprising submerging said lenses in an aqueous medium, adding to said aqueous medium a composition comprising, polyvinylpyrrolidone-hydrogen peroxide ($PVP-H_2O_2$) complex wherein said complex is in a solid form having an $H_2O_2$ component in an amount sufficient for said disinfecting, and a neutralizer component, in solid form, said neutralizer in an amount sufficient to substantially neutralize residual $H_2O_2$ from said disinfecting step. The $PVP-H_2O_2$ complex and neutralizer are contacted substantially simultaneously with said lenses submerged in said aqueous medium, and the neutralizer component may include means for delaying effective release of the neutralizer until after disinfecting has been achieved. The method of the invention provides significant cleaning and may include other cleaning compositions to aid cleaning of lenses, such as surfactants and proteolytic enzymes.

The lenses to be disinfected are submerged in an aqueous medium that is preferably a saline solution. The resulting solution is hypertonic and preserved. Other aqueous solutions may be used as desired so long as they are compatible with components of the invention.

DETAILED DESCRIPTION OF THE INVENTION

The preferred oxidizing component of the invention is a complex of polyvinylpyrrolidone (PVP) and hydrogen peroxide ($H_2O_2$). It is an anhydrous, uniform, free flowing fine white powder which may be stably mixed with other components of the composition of the invention. The complex may be about 5-40% by weight $H_2O_2$. A preferred $H_2O_2$ content is 15-25% $H_2O_2$ and 1-2% $H_2O$.

In general, the $PVP-H_2O_2$ complex is formed by suspending a PVP powder in a suitable anhydrous organic solvent, such as ethyl acetate, cyclohexane or the like. The $H_2O_2$ solution is prepared as an anhydrous solution wherein the anhydrous solvent is preferably the same solvent used to form the PVP suspension. The preferred solution is an anhydrous $H_2O_2$ solution having an $H_2O_2$ concentration in the range of about 20-50% by weight $H_2O_2$. The anhydrous $H_2O_2$ solution is slowly added to the cooled PVP suspension in an amount corresponding to the desired molar ratio of $PVP-H_2O_2$. Upon mixing the PVP suspension and anhydrous $H_2O_2$ solution, a fine white powder comprising the anhydrous $PVP-H_2O_2$ complex precipitates. The process of making the $PVP-H_2O_2$ complex, its stability and suitability as a soft lens disinfecting agent, is described by Merianos et al, in U.S. Pat. No. 5,008,106, which is incorporated herein by reference.

The neutralizer component of the invention may have, as its active ingredient, any of a number of compositions that neutralize or decompose oxidizing agents and, particularly, hydrogen peroxide to non-irritating water and oxygen. The neutralizing component may be a metal catalyst, as taught by Gaglia in U.S. Pat. No. 3,912,451, which uses metals of Groups 4, 5 or 6 of the Periodic Table. Useful metals include Pt, Pd, It, Rh, Re, Au, Ag, Cu, Cr, Os, Co, Fe, Mo, W, Mn, Ce or Th. Alternatively, the neutralizer component may be pyruvic acid, sodium pyruvate, sodium thiosulfate, thiourea, sodium sulfite, thioglycerol, sodium formate, ascorbic acid, oxalic acid or the like.

The neutralizer may also be an enzyme in a powder form. A preferred neutralizer component comprises catalase. Catalase is conventionally obtained from beef liver or microbial sources and has a crystalline structure. It is prepared for the present invention in a dry form by Sigma Chemical Co. of St. Louis, Mo. The catalase enzyme will decompose conventional 3% hydrogen peroxide within moments of contact with the hydrogen peroxide containing solution. The catalase component is particularly stable in its solid, substantially dry, form.

Both the PVP-$H_2O_2$ and catalase neutralizer are in solid form which may be combined in a single package for simultaneous delivery into an aqueous medium for holding the contact lenses to be disinfected. The ingredients must be packaged in a manner that prevents any significant premature reaction between the active components. The preferred package is a foiled pouch containing all of the disinfecting and neutralizing components in the absence of moisture.

The aqueous medium or solution in which disinfecting is carried out is preferably a saline solution that includes an effective preservative, such as sorbic acid or the like, such that lenses may be stored in the medium for long periods of time without having to re-disinfect. The disinfecting solution after neutralizing is a hypertonic solution of greater than 350 milliosmols per kilogram solution. Thus, the method further comprises rubbing and rinsing the disinfected lenses with a preserved isotonic saline solution prior to insertion of said lenses in the eye.

The aqueous medium saline solution may be formed of any soluble salt that is suitable for ophthalmic use and preferably includes sodium chloride, potassium chloride and mixtures thereof. Other alkali metal chlorides or alkaline earth metal chlorides such as calcium chloride and magnesium chloride can be used. Other suitable salts are sodium acetate, sodium sulfate, potassium sulfate, sodium tetraborate, sodium citrate, sodium phosphate, potassium phosphate or mixtures thereof may be used.

A preferred preservative for the saline solution is sorbic acid. Other ophthalmologically acceptable preservatives are edetate salts such as di-tri-, or tetra- sodium ethylene diamine tetracetate, polyhexamethylane biguanide, quaternary amines and others that are compatible with $H_2O_2$ as well as with the various contact lens materials.

A key advantage of the invention is that disinfecting of the lenses using the PVP-$H_2O_2$/neutralizer composition dissolved in a preserved saline finishes with the disinfectant lenses submerged in a preserved solution in which they may be held for long periods of time. Thus, there is no risk of re-infection with microbial agents since the solution in which the disinfected lenses is stored includes an antimicrobial agent or preservative. This is a key advantage over some prior art combinations, such as $H_2O_2$ solution disinfecting of lenses over a metal catalyst described by Gaglia in U.S. Pat. No. 3,912,451.

The neutralizer means of the invention may include a means for delaying release of neutralizer until after the disinfecting step is substantially complete. A preferred means for delaying release comprises encapsulating the neutralizer component in a capsule that remains substantially intact for a sufficient period of time to allow disinfecting and then subsequently disintegrates sufficiently to allow release of neutralizer component.

The delayed release means is preferably provided by means of a gelatin capsule containing a proteolytic enzyme and the neutralizing agent. The gelatin capsule containing the above-noted ingredients, when introduced into an aqueous medium, softens and swells but remains substantially intact for sufficient time to allow the disinfecting step to proceed. A sufficient amount of moisture from the aqueous medium at ambient temperatures, however, penetrates the capsule to dissolve the proteolytic enzyme which causes its activation. This process begins the digestion and subsequent disintegration of the gelatin capsule finally releasing the neutralizer, free to neutralize the oxidizing agent. The capsule may include a catalase neutralizing agent, subtilisin A proteolytic enzyme and a diluent, such as lactose, as a filler.

Other ingredients and excipients may also, of course, be included to ensure proper pH, tonicity and the like. Additional cleaning compositions, such as poloxamines and other surfactants, and proteolytic enzymes, such as subtilisin A and others may be included in the composition of the invention. The presence of the subtilisin A in the capsule, while primarily directed to causing delayed release of the neutralizer, also aids in removing protein from the lenses.

The following examples demonstrate the PVP-$H_2O_2$ neutralizer compositions and methods of disinfecting/cleaning of contact lenses of the invention.

EXAMPLE 1

Efficacy of PVP-$H_2O_2$ Dissolved in Preserved Saline Solution

A PVP-$H_2O_2$ complex supplied by ISP Technologies, Inc. of Wayne, N.J., as a uniform, free flowing fine white powder, is 18–22% by weight $H_2O_2$ and 1–2% by weight $H_2O$. Sufficient amounts of said complex are dissolved in an isotonic saline solution, preserved with sorbic acid to form solutions having 0.5–3% by weight $H_2O_2$.

Test volumes containing $10^6$ organisms/volume concentrations of test microorganisms are prepared for *Candida albicans* (Ca), *Aspergillus fumigatus* (Af) and *S. marcescens* (Sm) using standard culture methods, harvest techniques and quantitative microbiological analysis. Table I demonstrates efficacy of PVP-$H_2O_2$ described above.

TABLE I

| % $H_2O_2$ [wt %] | pH | Log Reduction of | | | | | |
|---|---|---|---|---|---|---|---|
| | | Sm | | Ca | | Af | |
| | | 1 hr | 4 hrs | 2 hr | 4 hrs | 2 hrs | 4 hrs |
| 3.0 | 5.9 | 1.7 | >4.5 | >4.4 | >4.4 | >4.9 | >4.9 |
| 2.0 | 6.1 | 1.1 | >4.5 | 2.9 | >4.4 | 3.4 | >4.9 |
| 1.0 | 6.5 | 0.8 | 2.3 | 1.2 | 1.9 | 0.6 | 2.3 |

EXAMPLE 2

(Controlled Release of Encapsulated Neutralizer and Resulting Residual $H_2O_2$)

A neutralizer component of the invention is formed by mixing and inserting into a gelatin capsule, the following solid components: catalase; subtilisin A or NaCl; and lactose filler. The gelatin capsule is manufactured by Capsagel, a division of Warner-Lambert Company of Greenwood, S.C. and characterized as Natual Conisnap ®.

The capsule is placed in an $H_2O_2$ solution generated by dissolving PVP-$H_2O_2$ solid in saline solution as described in Example 1 above. Table II reports residual $H_2O_2$ as a function of time (min.).

| Release Controlling Agent | Conc. of Agent (mg) | Conc. of Catalase Neutralizer (mg) | Percent Remaining $H_2O_2$ (%) v. time (min.) | | | | | |
|---|---|---|---|---|---|---|---|---|
| | | | 0 | 60 | 120 | 180 | 285 | 300 |
| a) subtilisin | 0.09 | 1.0 | 100 | 94.9 | 93.1 | ND | ND | 0 |
| b) NaCl | 70.00 | 1.4 | 100 | 44.1 | 27.0 | ND | ND | 0 |
| c) NaCl | 9.50 | 1.0 | 100 | 100.0 | — | 96.6 | 9.8 | ND |

Examples 2(b) and 2(c) demonstrate the effects that concentration of an inorganic salt decomposing agent has on the disinfecting environment. In Example 2(c) the concentration of NaCl is such that residual $H_2O_2$ remains substantially unaffected for about 180 minutes, before rapidly dropping to zero at about 285 minutes. In contrast, Example 2(b) shows a much faster release of neutralizer and rapid reduction of residual $H_2O_2$.

EXAMPLE 3

Efficacy of Controlled Release Disinfection System of the Invention

Gelatin capsules comprising the neutralizing component of the invention, identified as "Capsule 12" and containing: catalase, 1 mg; subtilisin, 2 mg; and lactose, 137 mg, are placed, substantially simultaneously with PVP-$H_2O_2$ complex, into a test sample of saline inoculated with the indicated test organism at a concentration of $10^6$ microorganisms/test volume. The samples are tested periodically over 6 hours for log reduction of microorganism population to determine efficacy.

TABLE III

| *Candida Albicans* - Log Reduction of Organism Population vs Time [hrs] | | | | |
|---|---|---|---|---|
| Sample | 1 hr | 2 hrs | 4 hrs | 6 hrs |
| Capsule 12 | 0.9 | 1.5 | 2.5 | 2.2 |

TABLE IV

| *Aspergillus fumigatus* - Log Reduction of Organism Population | | | | |
|---|---|---|---|---|
| | 1 hr | 2 hrs | 4 hrs | 6 hrs |
| Capsule 12 | 1.5 | 2.5 | 4.2 | 4.1 |

The above data shows efficacy of the system of the invention against difficult to kill microorganisms. In addition to the data shown in the tables, a greater than four log reduction was achieved for bacteria (Seratin Marcesens) in less than one hour.

EXAMPLE 4

Cleaning Efficacy of the PVP--$H_2O_2$ System of the Invention

The ability of the PVP-$H_2O_2$ disinfecting/neutralization systems to clean and remove protein deposit from contact lenses was assessed using an in-vitro model employing soft contact lenses, Softmate ® B (45% water, FDA Group III). Each contact lens was placed in a lens holder fitted to a vial for holding test solutions and components of the invention.

Each lens, in a lens holder, except for those lenses intended as blanks, was submerged in 5 ml of 0.1% lysozyme in a stock electrolyte solution adjusted to a pH of 7.2 and having an osmolality of about 300 ($\pm$20) mOsm/Kg. The electrolyte stock solution consisted of 0.7% sodium chloride, 0.2% potassium chloride, 0.2% sodium bicarbonate and 0.0005% calcium carbonate dissolved in distilled water. The lens vials holding the lenses and the lysozyme solution were then tightly closed and subjected to 80° C. for 20 minutes in a water bath. The lenses were allowed to cool overnight. Deposited lenses were then lightly rubbed and rinsed with saline solution (Sensitive Eyes ® Saline Solution manufactured by Bausch & Lomb of Rochester, N.Y.).

The in-vitro cleaning study experimental design required treating groups of 18 deposited or clean contact lenses following each six hour treatment regimen described below. Each treatment regimen required placing a lens, deposited with lysozyme or clean, in a lens holder and submerging the holder in the vial containing the test solution. The following test regimens were employed:

1. Deposited lenses were placed in a vial containing 10 ml of saline solution only;
2. Deposited lenses were placed in a vial containing 10 ml of saline solution, 1 g of PVP-$H_2O_2$ (2% hydrogen peroxide) and a neutralizer capsule A*;

*Composition of neutralizer Capsule A: catalase 1 mg; subtilisin A, 1mg; and lactose, 138 mg.

3. Deposited lenses were placed in a lens vial containing 10 ml of saline solution and 1 g of PVP-$H_2O_2$ (2% hydrogen peroxide) and a neutralizer capsule B**;

**Composition of the neutralizer Capsule B: catalase 1 mg; subtilisin, 1 mg; poloxamine surfactant, 50 mg; and lactose, 94 mg.

4. As control for experiment 2 above, undeposited clean lenses were placed in a lens vial containing 10 ml of saline solution, 1 g of PVP-$H_2O_2$ (2% hydrogen peroxide) and a neutralizer capsule A*;

*Composition of neutralizer Capsule A: catalase 1 mg; subtilisin A, 1mg; and lactose, 138 mg.

5. A control for experiment 3 above, undeposited clean lenses were placed in a lens vial containing 10 ml of saline solution, 1 g of PVP-$H_2O_2$ (2% hydrogen peroxide) and a Capsule B**;

**Composition of the neutralizer Capsule B: catalase 1 mg; subtilisin, 1 mg; poloxamine surfactant, 50 mg; and lactose, 94 mg.

6. Deposited lenses were placed in a lens vial containing 10 ml of saline solution and 1 g of PVP-$H_2O_2$ (2% hydrogen peroxide); and 7. As a control for experiment 6 above, undeposited clean lenses were placed in a lens vial containing 10 ml of saline solution and 1 g of PVP-H$_2$O$_2$ (2% hydrogen peroxide).

In each of the above regimens, the lenses were allowed to stand for six hours and the amount of protein remaining on the lenses was determined. The protein determinations were made by digesting each lens in 1 ml of aqueous 2.5N sodium hydroxide in a culture test tube at 100° C. for two hours, followed by cooling. 150 ml of the hydrolysate were transferred to a test tube to which were added 50 ml of gacial acetic acid to neutralize the hydrolysate, followed by adding 400 ml of ninlydrin reagent. The solution was heated in a water bath at 90° C. for 20 minutes and immediately cooled in a ice bath. The cooled solutions were diluted and mixed with 1 ml of 1-to-1 isopropyl alcohol/distilled water. The absorbance of each sample at 570 nm was measured to determine the amount of lysozyme remaining on the lenses by comparing with standard curves.

The amount of protein remaining on the lenses was determined by substracting the control readings and statistically comparing the differences with Regimen #1 wherein the deposited lenses were only soaked in saline solution. Table V reports the results of the experiment.

TABLE V

| Regimen | Amount of Protein Remaining |
|---|---|
| Regimen #1 | 62.2 μg |
| Regimen #2 | 42.2 μg |
| Regimen #3 | 45.2 μg |
| Regimen #4 | 43.2 μg |

A statistical analysis of the resulting data shows that at 0.05 significance level, the regimen treatments #2, #3 and #6 are significantly different from the results of Regimen treatment #1. This clearly demonstrates the cleaning efficacy of the PVP-H$_2$O$_2$ and the PVP-H$_2$O$_2$ neutralizer systems of the invention for removing protein material.

In operation, solid PVP-H$_2$O$_2$ and powdered or encapsulated neutralizer are added, substantially simultaneously, to an isotonic saline solution, preferably preserved, for holding the lenses. The PVP-H$_2$O$_2$ dissolves, producing an H$_2$O$_2$ concentration of 3% or less by weight H$_2$O$_2$ preferably about 2% by weight H$_2$O$_2$ or less. The contact lenses are then submerged in the H$_2$O$_2$ solution which effectively disinfects the lenses. The required time for completion of disinfecting varies depending upon the concentration of the H$_2$O$_2$ and other factors. Where the neutralizer is encapsulated in the preferred gelatin capsule delayed release system, in response to the water content of the lens holding solution, water is transmitted through the walls of the gelatin capsule. The water activates the proteolytic enzyme or inorganic salt present within the capsule initiating disintegration of the capsule walls. Depending upon the excipients present within the capsule, the disintegration or decomposing process, releasing neutralizing component, is delayed for a time sufficient to permit disinfection of the lenses. The neutralizer component, preferably catalase, is then released. The catalases, within minutes, begins to reduce the H$_2$O$_2$ level of the disinfecting solution and, ultimately, decomposition reduces the residual level to that which can be accommodated by the eye. The resulting solution is a hypertonic solution having an osmolality of greater than 350 milliosmols/kg solution. A rub and rinse of the lenses with isotonic saline is typically done before the lenses are inserted into the eye.

A preferred regimen is as follows:
1. Remove lenses from the eye
2. Rub and rinse with preserved saline
3. Place lenses in a lens holder
4. Transfer contents of the packet containing solid PVP-H$_2$O$_2$ complex and neutralizer capsule to a lens holder vial
5. Add 10 ml of preserved saline to the vial, dissolving the components of step 4
6. Place the lens holder containing the lenses in the vial
7. Allow to soak for up to 6 hours
8. Remove lenses and rinse with preserved saline before inserting in the eye It will be evident to those skilled in the art that the combination of solid PVP-H$_2$O$_2$ and solid neutralizer component is useful with any type of solid neutralizer component, preferably a controlled release composition for controlled release of the neutralizer agent into the disinfecting solution.

I claim:

1. A preserved saline solution for disinfecting and cleaning contact lenses, comprising:

A solid PVP-H$_2$O$_2$ complex; and a solid neutralizer component for neutralizing H$_2$O$_2$ after disinfecting, wherein said neutralizer component comprises a gelatin capsule of sufficient integrity for holding said neutralizing component and delaying release of said neutralizer component for a predetermined amount of time determined by said capsule integrity, and said gelatin capsule includes within said capsule a decomposing agent that is activated by moisture passing into said capsule as it swells such that said decomposing agent disintegrates said capsule releasing said neutralizing agent.

2. The preserved saline solution of claim 1 further comprising a preservative, wherein said preservative is sorbic acid, edetate salts of ethylene diamine tetracetate, polyhexamethylene biquamide or quaternary amines.

3. The preserved saline solution of claim 1 wherein said neutralizer component is a metal catalyst of Groups 4, 5 and 6 of the Periodic Table.

4. The preserved saline solution of claim 3 wherein said metal is of Pt, Pd, It, Rh, Re, Au, Ag, Cu, Cr, Os, Co, Fe, Mo, W, Mn, Ce or Th.

5. The preserved saline solution of claim 1 wherein said neutralizing component is pyruvic acid or sodium pyruvate.

6. The preserved saline solution of claim 1 wherein said neutralizer component is sodium thiosulfate, thiourea, sodium sulfite, or ascorbic acid.

7. The preserved saline solution of claim 1 wherein said neutralizer component is an enzyme of catalase or peroxidase.

8. The preserved saline solution of claim 1 wherein said decomposing agent is a proteolytic enzyme.

9. The preserved saline solution of claim 1 wherein said decomposing agent is a salt that, upon contact with said moisture, causes an osmotic gradient that induces flow of aqueous medium into said capsule causing its disintegration and release of said neutralizing agent.

10. A method for disinfecting and cleaning contact lenses, comprising:

contacting said lenses with an aqueous saline solution that includes a preservative; and contacting said lenses in said solution with a composition comprising a solid PVP-$H_2O_2$ complex and a solid neutralizer component for neutralizing $H_2O_2$, wherein said neutralizer component comprises a gelatin capsule of sufficient integrity for holding said neutralizing component and delaying release of said neutralizer component for a predetermined amount of time determined by said capsule integrity, and said gelatin capsule includes within said capsule a decomposing agent that is activated by moisture passing into said capsule as it swells such that said decomposing agent disintegrates said capsule releasing said neutralizing agent, wherein said lenses are disinfected, residual $H_2O_2$ is neutralized and said disinfected lenses remain in a preserved solution.

11. The method of claim 10 wherein said neutralizing component is catalase or peroxidase, said decomposing agent is a proteolytic enzyme or a salt, and the solution is hypertonic.

* * * * *